United States Patent [19]
Haugland et al.

[11] Patent Number: 5,442,045
[45] Date of Patent: Aug. 15, 1995

[54] BIOLOGICAL CONJUGATES OF FLUORESCENT RHODOL DYES

[75] Inventors: Richard P. Haugland; James E. Whitaker, both of Eugene, Oreg.

[73] Assignee: Molecular Probes, Inc., Eugene, Oreg.

[21] Appl. No.: 28,319

[22] Filed: Mar. 8, 1993

Related U.S. Application Data

[62] Division of Ser. No. 509,360, Apr. 16, 1990, Pat. No. 5,227,487.

[51] Int. Cl.⁶ .............. G01N 37/00; C07K 1/13; C07D 211/00
[52] U.S. Cl. .............. 530/391.3; 530/402; 536/25.32; 536/26.6
[58] Field of Search .............. 544/150; 546/41; 548/417; 549/390, 391; 530/391.1, 391.3, 402; 536/25.32, 26.6

[56] References Cited
PUBLICATIONS

Whitaker et al., Anal. Biochem., 1992, 207:267.
Goding et al., Monoclonal Ab., Principles & Practice, pp. 241–248.

*Primary Examiner*—David L. Lacey
*Assistant Examiner*—F. Christopher Eisenschenk
*Attorney, Agent, or Firm*—Allegra J. Helfenstein; Anton E. Skaugset

[57] ABSTRACT

Novel fluorescent dyes based on the rhodol structure are provided. The new reagents contain functional groups capable of forming a stable fluorescent product with functional groups typically found in biomolecules or polymers including amines, phenols, thiols, acids, aldehydes and ketones. Reactive groups in the rhodol dyes include activated esters, isothiocyanates, amines, hydrazines, halides, acids, azides, maleimides, aldehydes, alcohols, acrylamides and haloacetamides. The products are detected by their absorbance or fluorescence properties. The spectral properties of the fluorescent dyes are sufficiently similar in wavelengths and intensity to fluorescein or rhodamine derivatives as to permit use of the same equipment. The dyes, however, show less spectral sensitivity to pH in the physiological range than does fluorescein, have higher solubility in non-polar solvents and have improved photostability and quantum yields.

20 Claims, 8 Drawing Sheets

BIOLOGICAL CONJUGATES OF FLUORESCENT RHODOL DYES

This work was supported in part by DOE grant DE-FG06-88ER-60684. The government has certain rights to this invention.

This application is a division of Application Ser. No. 07/509,360, filed April 16, 1990, which has issued as U.S. Pat. No. 5,227,487.

FIELD OF THE INVENTION

This invention is related to improvements in dyes that are useful as fluorescent tracers. Specifically, the improvements relate to chemically reactive dyes that can be reacted with ligands to give conjugates with fluorescence properties sufficiently similar to fluorescein or rhodamine dyes so that the same equipment can be used but with unique spectral and chemical advantages.

BACKGROUND OF THE INVENTION

Fluorescent dyes are widely used as tracers for localization of biological structures by fluorescence microscopy, for quantification of analytes by fluorescence immunoassay, for flow cytometric analysis of cells, for measurement of physiological state of cells, for quantitative assays such as DNA sequencing and other applications [Y. Kanaoka, Angew Chem. Intl. Ed. Engl. 16, 137 (1977); I. Hemmila. Clin. Chem. 31,359 (1985)]. Their primary advantages over other types of absorption dyes include visibility of the emission at a wavelength distinct from the excitation, the orders of magnitude greater detectability of fluorescence emission over light absorption, the generally low level of fluorescence background in most biological samples and the measurable intrinsic spectral properties of fluorescence polarization [M. E. Jolley, et al. Clin. Chem. 27, 1190 (1981)], lifetime and excited state energy transfer [U.S. Pat. No. 3,996,345].

For many applications that utilize fluorescent dyes as tracers, it is necessary to chemically react the dye with a biologically active ligand such as a cell, tissue, protein, antibody, enzyme, drug, hormone, nucleotide, nucleic acid, polysaccharide, lipid or other biomolecule to make a fluorescent ligand analog or with natural or synthetic polymers. With these synthetic probes the biomolecule frequently confers a specificity for a biochemical interaction that is to be observed and the fluorescent dye provides the method for detection and/or quantification of the interaction.

Chemically reactive synthetic fluorescent dyes have long been recognized as essential for following these interactions [A. H. Coons & M. H. Kaplan, J. Exp. Med. 91, 1 (1950); E. Soini & I. Hemmila. Clin. Chem. 25, 353 (1979)]. The fluorescent dyes currently used to prepare useful conjugates are limited to a relatively small number of aromatic structures. Reactive fluorescein and rhodamine derivatives have been by far the most commonly used fluorescent dyes for preparation of fluorescent conjugates that can be excited and detected at wavelengths longer than 480 nm. The spectral properties that are most useful in a dye are frequently limited by the principal excitation wavelengths available in the common light sources. Primary among these are the argon laser and the mercury arc lamp which are used in many of the most sensitive applications of fluorescent probes. Certain intrinsic properties of the known fluorescent dyes, that include absorbance and fluorescence yield, stability during illumination and sensitivity of the spectra to the environment, limit the suitability of current dyes, including the fluoresceins and rhodamines, particularly in quantitative applications. It is the object of this invention to provide improved fluorescent dyes. It is further an object of this invention to provide dyes with the chemical reactivity necessary for conjugation to a variety of the functional groups commonly found in biomolecules, drugs, and natural and synthetic polymers.

The useful dyes would have the following properties:

1. A high absorbance as measured by extinction coefficient and a high fluorescence quantum yield with a relatively narrow emission peak.
2. High absorbance at the most intense emission lines of the common excitation sources such as the 488 nm and 514 nm lines of the argon ion laser, the 546 nm line of the mercury arc lamp and the 543 nm and 632 nm lines of the helium-neon laser.
3. High solubility of the dye and its reactive derivatives in a variety of solvents to maximize the utility of the dye for modification of cells, biopolymers and other ligands of interest and a low tendency of the labelled ligands or biomolecules to aggregate.
4. High stability of the dye to excitation light, enhancing the utility of the dye for quantitative measurements and permitting extended illumination time and higher lamp intensities for increased sensitivity.
5. For quantitative measurements, low sensitivity of the emission intensity to properties of the solution is necessary so that the measured signal is proportional only to the absolute quantity of dye present and is relatively independent of environmental effects such as pH, viscosity and polarity.
6. Suitability of the dye for preparation of reactive derivatives of several different types which exhibit direct chemical reactivity toward a variety of the chemically reactive sites typically found in biomolecules and other ligands of interest.
7. Intrinsically low biological activity or toxicity of the dye.

Coons and Kaplan in 1950 first prepared a chemically reactive isocyanate of fluorescein and later J. L. Riggs. et al. [Am. J. Pathol. 34, 1081 (1958)] introduced the more stable isothiocyanate analog of fluorescein. Fluorescein isothiocyanate (FITC) remains one of the most widely used tracers for fluorescent staining and immunoassay. Other reactive fluoresceins were prepared by Haugland [U.S. Pat. No. 4,213,904]. Virtually all fluorescence microscopes are equipped with excitation sources and filters optimized to excite and detect fluorescein emission. Due to the intense but discrete excitation of the argon laser at 488 nm which is strongly absorbed by the primary fluorescein absorption band (maximum at 492 nm), fluorescein has also become the primary dye for use in the techniques of flow cytometry [L. L. Lanier & M. R. Loken, J. Immunol. 132, 151 (1984)] and laser scanning microscopy. There is a recognized need for suitable fluorophores for applications in multi-color microscopy [H. Khalfan, et al., Histochem. J. 18, 497 (1986)], flow cytometry [Stryer, et al., U.S. Pat. No. 4,520,110; J. A. Titus, et al., J. Immunol. Methods 50, 193 (1982)], immunoassays [W. A. Staines, et al., J. Histochem. Cytochem. 36, 145 (1988)], and DNA sequencing [L. M. Smith, et al. Nature 321,674 (1986)]. Multicolor fluorescence typically has employed fluorescein in combination with longer wavelength dyes such as the fluorescein derivatives eosin isothiocyanate [R. J. Cherry, *FEBS Lett.* 55, 1 (1975)], erythrosin isothiocyanate [C. J. Restall, *Biochim. Biophys. Acta* 670, 433 (1981)], chloro and methoxy substituted fluoresceins [U.S. Pat. No. 4,318,846] as well as rhodamine derivatives, such as tetramethylrhodamine isothiocyanate [J. A. Gourlay & J. R. Pemberton, *Appl. Microbiol.* 22, 459 (1971)], 5(6)-carboxytetramethylrhodamine, succinimidyl ester [P. L. Khanna, & E. F. Ullman, *Anal. Biochem* 108, 156 (1980)], X-rhodamine isothiocyanate [H. A. Crissman & J. A. Steinkemp, *Cytometry* 3, 84 (1982)], carboxy-X-rhodamine, succinimidyl ester [G. P. A. Vigers, et al., *J. Cell Biol.* 107, 1011 (1988)], Lissamine rhodamine B sulfonyl chloride [C. S. Chadwick, et al., *Immunology* 1,315 (1958)] and Texas Red [J. A. Titus, R. P. Haugland, S. O. Sharrow, *J. Immunol. Methods* 50, 193 (1982)].

The primary advantages that have permitted fluorescein isothiocyanate and its conjugates to remain the standard for microscopy and fluorescence immunoassay are high absorptivity, a high quantum yield and general ease of conjugation to biomolecules. The only fluorescent tracers in common use that exceed the overall fluorescence yield of fluorescein on a molar basis are the phycobiliproteins [U.S. Pat. No. 4,520,110; V. T. Oi, et al. *J. Cell Biol.* 93, 981 (1982); M. N. Kronick & P. D. Grossman, *Clin. Chem.* 29, 1582 (1983)]. These require special methods for conjugation to biomolecules and in some cases such as fluorescence polarization immunoassays [M. E. Jolley, et al., *Clin. Chem.* 27, 1190 (1981)] have too high a molecular weight to be useful. Phycobiliproteins also have high susceptibility to photodegradation [J. C. White & L. Stryer, *Analyt. Biochem.* 161,442 (1987)]. The only chemically reactive fluorophores with spectra similar to fluorescein that have been described are derived from the nitrofurazan structure [Soini and Hemilla (1979)] and the dipyrromethenboron difluoride structure [Haugland and Kang, U.S. Pat. No. 4,774,339; Monsma, et al., *J. Neurochem.* 52, 1641 (1989)]. The nitrofurazan derivatives have much weaker absorptivity (less than 25,000 cm$^{-1}$ M$^{-1}$ at its peak at 468 NM versus 75,000 cm$^{-1}$ M$^{-1}$ for fluorescein at its peak near 490 NM) and virtually no fluorescence in aqueous solutions, where fluorescein is usually used, and where most applications in immunofluorescence exist. The dipyrromethenboron difluoride dyes, while possessing high extinction coefficients and quantum yields, are less photostable and more hydrophobic than the subject fluorophores.

Despite their widespread acceptance as fluorescent tracers, derivatives of fluorescein and the recently introduced derivatives of dipyrromethenboron difluoride have some deficiencies that preclude or make more difficult some useful applications. Primary is the strong tendency of the fluorophores to photobleach when illuminated by a strong excitation source such as the mercury or xenon arc lamps typically used in fluorescence microscopes. The photobleaching can result in a significant percentage of the fluorescence being lost within seconds of the onset of illumination. In fluorescence microscopy this results in loss of the image. In fluorescence assays, the loss of fluorescence with time makes quantification of results difficult and ultimately decreases the sensitivity of detection of the analyte. To a variable degree, extrinsic reagents including propyl gallate and p-phenylenediamine retard, but do not eliminate, the photobleaching. However, these anti-fade agents cannot be used in experiments with living cells, one of the major recent applications of fluorescent dyes and fluorescently labelled ligands. Additionally, fluorescein and its derivatives show a pH dependent absorption spectrum that decreases the fluorescence yield in solutions at physiological pH or below. Furthermore, in applications requiring simultaneous excitation of two or more dyes whose emission is to be quantified separately, it is often more desirable to use the 514 nm line of the argon ion laser, since the extinction coefficient of the commonly used long wavelength dyes such as tetramethylrhodamine, rhodamine B and Texas Red is considerably higher at 514 nm than at 488. The absorption intensity of fluorescein at 514 nm is less than 10% of its maximum intensity at 492 nm and shows proportionally lower fluorescence intensity when excited at 514 nm.

In addition to the 488 nm and 514 nm lines of the argon ion laser, other significant, intense excitation wavelengths available from common sources are the 532 nm line of the Nd:YAG laser and the 546 nm line of the mercury arc lamp as well as the 543 nm and 632 nm lines of helium neon lasers. Since the sensitivity of detection of fluorescent ligands is proportional to the product of the lamp intensity, the absorbance and the quantum yield, dyes having significant absorbance and fluorescence at these longer wavelengths, such as some of the dyes which are the subject of this invention, are also useful. By far the most common reactive dye in current use that can be excited at these wavelengths has been tetramethylrhodamine, commonly used as its isothiocyanate derivative, TRITC.

Tetramethylrhodamine, while pH insensitive and relatively photostable, possesses several deficiencies which limit its utility as a fluorescent label. Primary among these is the relatively low quantum yield of the dye in aqueous solution. While the quantum yield of tetramethylrhodamine in alcohol is above 0.90, the quantum yield in water drops to approximately 0.23, which decreases the sensitivity of detection concomitantly. Protein conjugates of tetramethylrhodamine show a further decrease in fluorescence quantum yield and exhibit complex absorption behavior resulting from the tendency of rhodamine derivatives to aggregate in aqueous solution [O. Valdes-Aguilera & D. C. Neckers, *Acc. Chem. Res.* 22, 171 (1989)]. Another drawback of tetramethylrhodamine is the high sensitivity of emission to solvent polarity and viscosity. Additionally, the low water solubility of reactive forms of the dye and its conjugates present difficulties for the preparation and use of rhodamine labelled probes.

Clearly there is a need and opportunity for more fluorescent and more photostable reactive fluorophores. The base for the new chemically reactive fluorophores of this invention is a rhodol compound. While a number of substituted and unsubstituted derivatives of the parent heterocyclic compound have been described [I. S. Ioffe & V. F. Otten, *J. Org. Chem. USSR* 1,326-336 (1965); G. A. Reynolds, U.S. Pat. No. 3,932,415; L. G. Lee, et al., *Cytometry* 10, 151 (1989)], their research did not provide methods whereby the fluorophores could be chemically reacted with ligands.

SUMMARY OF THE INVENTION

Novel reactive fluorescent tracers are described that have the combination of fluorescein or rhodamine-like spectra, direct chemical reactivity with the functional groups present in ligands typically combined with fluorescent tracers, low sensitivity of spectra to solution pH in the physiological range, high quantum yields and high photostability. The subject materials of this invention have fluorescence properties sufficiently similar to the fluorescein and rhodamine derivatives in common use that they can use the same optical equipment as is used with fluorescein- and rhodamine-based tracers without modification of the excitation sources or optical filters. Additionally, some examples are more ideally suited than existing dyes for multicolor applications at intermediate wavelengths. In most cases, the dyes show significantly higher photostability than fluorescein without addition of external stabilizing agents. They exhibit lower sensitivity of fluorescence emission to pH than does fluorescein and, of major importance, have emission yields comparable to or better than the fluorescein and rhodamine derivatives currently employed as fluorescent labels. Some of the reactive derivatives lack ionic charge and, in general, the dyes and their conjugates have a broad range of solubility including polar and non-polar solvents.

In summary, the reactive dyes which are the subject of this invention exhibit a number of useful properties, namely:

1. Stokes' shifts, absorption and emission bandwidths and quantum yields comparable to fluorescein and rhodamine derivatives.
2. High extinction coefficients, quantum yields and photostabilities.
3. High solubility in a variety of solvents.
4. Low sensitivity to pH, solvent polarity and other environmental effects.
5. Reactivity with many of the functional groups found in biomolecules.
6. Compatibility with common excitation sources.

DETAILED DESCRIPTION OF SPECIFIC EMBODIMENTS

1. General Properties

Figure 1A:
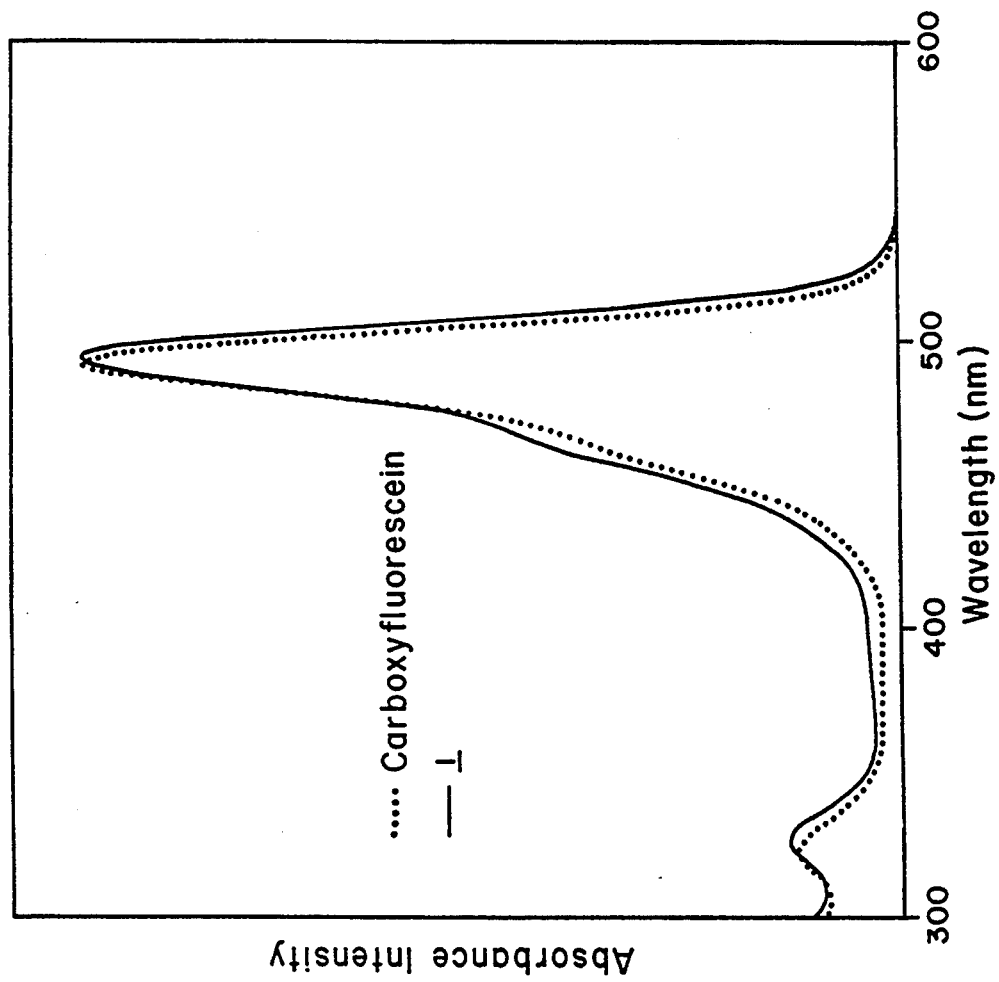
FIG. 1a shows the absorption spectra of dye 1 and carboxyfluorescein in 50 mM potassium phosphate buffer at pH 8.0.

The subject invention describes novel, chemically reactive rhodol derivatives and methods for synthesis of reactive derivatives of these fluorophores. Furthermore, it is demonstrated that the materials can be chemically bonded to the functional groups present in many biomolecules to form fluorescent ligand analogs or polymeric materials for use as fluorescent tracers. Potentially reactive functional groups intrinsically present or that can be introduced into biomolecules and polymers include, but are not limited to, amines, thiols, alcohols, carboxylic acids, aldehydes, and ketones. Chemically reactive fluorescent reagents have been developed in this invention for modification of all of these functional groups under conditions of solvent, temperature and pH that usually do not destroy the biological activity of the modified biomolecule. None of the reagents previously described in the chemical or biochemical literature are recognized as possessing the appropriate combination of chemical reactivity, spectra, high photostability, fluorescence yield and low pH sensitivity that are properties of the dyes of this invention to make them useful reactive alternatives to fluoresceins and rhodamines.

The new derivatives of the rhodol heterocycle that are the subject of this invention have the general structures below.

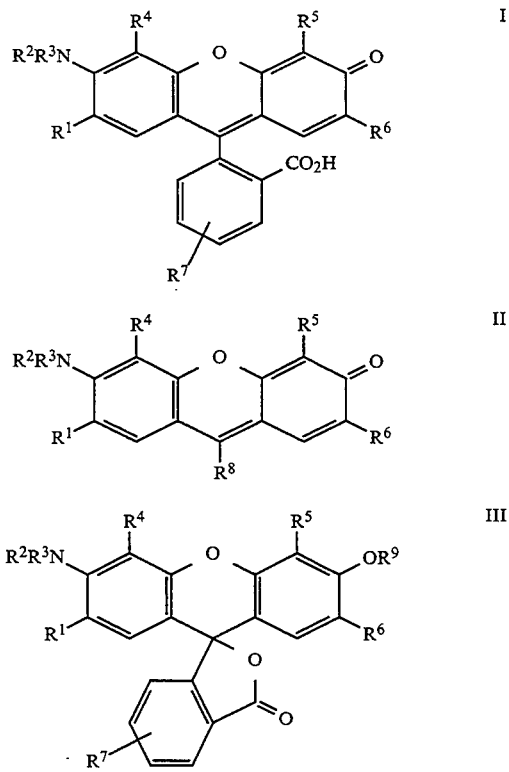

In these structures, $R^1$, $R^4$, $R^5$ and $R^6$ are H, alkyl, carboxyalkyl, aminoalkyl, halogen or alkoxy; $R^2$ and $R^3$ are H, alkyl, carboxyalkyl, aminoalkyl or trifluoroacetyl; $R^7$ is H, alkyl, aryl, carboxy, nitro, amino or substituted amino or sulfo or reactive derivatives of these groups. $R^8$ is H, alkyl, aryl, carboxy, carboxyalkyl, aminoalkyl, cyano, perfluoroalkyl, or haloalkyl and $R^9$ is H, alkyl or acyl. Furthermore, $R^1$ and $R^2$, $R^2$ and $R^3$, and $R^3$ and $R^4$ may be joined so as to form one or two 5- or 6-membered rings which may contain an oxygen or nitrogen atom. $R^6$ and $R^9$ may be joined to form a six-membered lactone ring. At least one of the substituents $R^1$, $R^2$, $R^3$, $R^4$, $R^5$, $R^6$, $R^7$, or $R^8$ is further modified to provide a chemically reactive functional group. It is also possible to introduce protecting groups such as acetates and trifluoroacetamides which can be removed subsequent to conjugation or which increase the membrane permeability of the reactive dyes [J. A. Thomas, et al., *Biochemistry* 18, 2210 (1979)]. Some of the reactive functional groups of the rhodol dyes that have been prepared and the functional groups with which they are commonly reactive are listed in Table 1. The tabulation is not meant to be inclusive of chemical reactivity since with the appropriate choice of solvent, temperature and catalysts, other functional groups can be made to react and the listed functional groups can be made to react with other reactive sites.

TABLE 1

| REACTIVE FUNCTION | REACTIVE SITES |
| --- | --- |
| succinimidyl esters | amines, thiols |
| acyl azides | amines, thiols |
| isothiocyanates | amines, thiols, alcohols, phenols |
| hydrazines | aldehydes, ketones, acid derivatives |
| amines | carboxylic acids, halides, aldehydes and ketones |
| haloacetamides | thiols, imidazoles, phenols, amines |
| alcohols | acid derivatives |
| halides | alcohols, amines, thiols, carboxylic acids |
| imido esters | amines |
| azides | photoaffinity reagents |
| acrylamides | olefins |
| maleimides | thiols, amines |

Chemically reactive derivatives of fluorophores have wide utility as tracers and in the preparation of fluorescent derivatives of other molecules for use as tracers. This invention describes methods for preparation of rhodol dyes that incorporate carboxylic acids and esters, amines, azides, hydrazides, halides, alcohols and aldehydes and their subsequent modification to give chemically reactive reagents that can be coupled to other molecules for use as fluorescent tracers. Several examples of derivatives that have the chemical structures and properties claimed by this invention and the precursors that are used in their synthesis are listed in Table 2.

TABLE 2

EXAMPLES OF SUBSTITUENTS OF NEW RHODOL DYES[a]

| Dye | $R^1$ | $R^2$ | $R^3$ | $R^4$ | $R^5$ | $R^6$ | $R^7$ | $R^8$ | $R^9$ |
| --- | --- | --- | --- | --- | --- | --- | --- | --- | --- |
| 1 | H | H | H | H | H | H | $CO_2H$ | — | — |
| 2 | H | H | $CF_3CO$ | H | H | H | $CO_2Succ.$ | — | — |
| 3 | H | $CF_3CO$ | H | H | H | H | $CO_2H$ | — | — |
| 4 | H | $CF_3CO$ | H | H | H | H | $CO_2Succ.$ | — | — |
| 5 | Cl | H | H | H | Cl | H | $CO_2H$ | — | — |
| 6 | Cl | H | H | H | Cl | Cl | $CO_2H$ | — | — |
| 7 | $CH_3$ | $C_2H_5$ | H | H | H | H | $CO_2H$ | — | — |
| 8 | $CH_3$ | $C_2H_5$ | H | H | H | Cl | $CO_2H$ | — | — |
| 9 | $CH_3$ | $C_2H_5$ | H | H | H | Cl | $CO_2Succ.$ | — | — |
| 10 | $CH_3$ | $C_2H_5$ | H | H | H | Cl | $CONH(CH_2)_2OH$ | — | — |
| 11 | $CH_3$ | $C_2H_5$ | H | H | H | Br | $CO_2H$ | — | — |
| 12 | $CH_3$ | $C_2H_5$ | H | H | H | $CH_3$ | $CO_2H$ | — | — |
| 13 | $CH_3$ | $C_2H_5$ | H | H | H | $CH_3$ | $CO_2Succ.$ | — | — |
| 14 | $CH_3$ | $C_2H_5$ | H | H | H | $C_2H_5$ | $CO_2H$ | — | — |
| 15 | $CH_3$ | $C_2H_5$ | H | H | H | $C_2H_5$ | $CO_2Succ.$ | — | — |
| 16 | $CH_3$ | $C_2H_5$ | H | H | $CH_3$ | H | $CO_2H$ | — | — |
| 17 | $CH_3$ | $C_2H_5$ | H | H | H | $(CH_2)_2CO_2H$ | H | — | — |
| 18 | $CH_3$ | $C_2H_5$ | H | H | H | Cl | $NO_2$ | — | — |
| 19 | H | $CH_3$ | $CH_3$ | H | H | H | $CO_2H$ | — | — |
| 20 | H | $C_2H_5$ | $C_2H_5$ | H | H | H | $CO_2H$ | — | — |
| 21 | H | $R^2 + R^3 = (CH_2)_2O(CH_2)_2$ | | H | H | H | $CO_2H$ | — | — |
| 22 | $R^1 + R^2 = (CH_2)_3$ | | H | H | H | H | $CO_2H$ | — | — |
| 23 | $R^1 + R^2 = (CH_2)_3$ | | H | H | H | H | $CO_2Succ.$ | — | — |
| 24 | $R^1 + R^2 = (CH_2)_3$ | | H | H | H | Cl | $CO_2H$ | — | — |
| 25 | $R^1 + R^2 = (CH_2)_3$ | | H | H | H | Cl | $CO_2Succ.$ | — | — |
| 26 | $R^1 + R^2 = (CH_2)_3$ | | $R^3 + R^4 = (CH_2)_3$ | | H | H | $CO_2H$ | — | — |
| 27 | $R^1 + R^2 = (CH_2)_3$ | | $R^3 + R^4 = (CH_2)_3$ | | H | H | $CO_2Succ.$ | — | — |
| 28 | $R^1 + R^2 = (CH_2)_3$ | | $R^3 + R^4 = (CH_2)_3$ | | H | Cl | $CO_2H$ | — | — |
| 29 | $R^1 + R^2 = (CH_2)_3$ | | $R^3 + R^4 = (CH_2H_3$ | | H | Cl | $CO_2Succ.$ | — | — |
| 30 | $R^1 + R^2 = (CH_2)_3$ | | $R^3 + R^4 = (CH_2)_3$ | | H | Cl | $CONH(CH_2)_5NH_2$ | — | — |
| 31 | $R^1 + R^2 = (CH_2)_3$ | | $R^3 + R^4 = (CH_2)_3$ | | H | Cl | $CONH(CH_2)_2NH_2$ | — | — |
| 32 | $R^1 + R^2 = (CH_2)_3$ | | $R^3 + R^4 = (CH_2)_3$ | | H | Br | $CO_2H$ | — | — |
| 33 | $R^1 + R^2 = (CH_2)_3$ | | $R^3 + R^4 = (CH_2)_3$ | | H | $C_2H_5$ | $CO_2H$ | — | — |
| 34 | $R^1 + R^2 = (CH_2)_3$ | | $R^3 + R^4 = (CH_2)_3$ | | H | $(CH_2)_{15}CH_3$ | $CO_2H$ | — | — |
| 35 | $R^1 + R^2 = (CH_2)_3$ | | $R^3 + R^4 = (CH_2)_3$ | | $CH_2NH$—$COCH_2Cl$ | H | H | — | — |
| 36 | $R^1 + R^2 = (CH_2)_3$ | | $R^3 + R^4 = (CH_2)_3$ | | $CH_2NH_2.HCl$ | H | H | — | — |
| 37 | $R^1 + R^2 = (CH_2)_3$ | | $R^3 + R^4 = (CH_2)_3$ | | $CH_2NH$—$COCH_2Cl$ | H | $CO_2H$ | — | — |
| 38 | $R^1 + R^2 = (CH_2)_3$ | | $R^3 + R^4 = (CH_2)_3$ | | $CH_2NH_2.HCl$ | H | $CO_2H$ | — | — |
| 39 | $R^1 + R^2 = (CH_2)_3$ | | $R^3 + R^4 = (CH_2)_3$ | | H | $(CH_2)_2CO_2H$ | H | — | — |
| 40 | $R^1 + R^2 = (CH_2)_3$ | | $R^3 + R^4 = (CH_2)_3$ | | H | $(CH_2)_4CO_2H$ | H | — | — |
| 41 | $R^1 + R^2 = (CH_2)_3$ | | $R^3 + R^4 = (CH_2)_3$ | | H | $(CH_2)_{11}CO_2H$ | H | — | — |
| 42 | $R^1 + R^2 = (CH_2)_3$ | | $R^3 + R^4 = (CH_2)_3$ | | H | $(CH_2)_2CONH$—$(CH_2)_5NHCOCH:CH_2$ | H | — | — |
| 43 | $R^1 + R^2 = (CH_2)_3$ | | $R^3 + R^4 = (CH_2)_3$ | | H | $(CH_2)_2CONH$—$(CH_2)_5NHCOC_6H_4N_3$ | H | — | — |
| 44 | $R^1 + R^2 = (CH_2)_3$ | | $R^3 + R^4 = (CH_2)_3$ | | H | $(CH_2)_2CONH$—$(CH_2)_5NHCOCH_2I$ | H | — | — |
| 45 | $R^1 + R^2 = (CH_2)_3$ | | $R^3 + R^4 = (CH_2)_3$ | | H | $(CH_2)_2CONH$—$(CH_2)_5NHCOCH_2$— | H | — | — |

TABLE 2-continued
EXAMPLES OF SUBSTITUENTS OF NEW RHODOL DYES[a]

| Dye | $R^1$ | $R^2$ | $R^3$ | $R^4$ | $R^5$ | $R^6$ | $R^7$ | $R^8$ | $R^9$ |
|---|---|---|---|---|---|---|---|---|---|
| 46 | $R^1 + R^2 = (CH_2)_3$ | | $R^3 + R^4 = (CH_2)_3$ | | H | NCOCH:CHCO $(CH_2)_2CONH-$ $(CH_2)_5NHCO-$ $C_6H_4CHO$ | H | — | — |
| 47 | $R^1 + R^2 = (CH_2)_3$ | | $R^3 + R^4 = (CH_2)_3$ | | H | $(CH_2)_2CONH-$ $(CH_2)_5NHCO-$ $(CH_2CHCO_2H)-$ $SCOCH_3$ | H | — | — |
| 48 | $R^1 + R^2 = (CH_2)_3$ | | $R^3 + R^4 = (CH_2)_3$ | | H | $(CH_2)_2CO_2H$ | $CO_2H$ | — | — |
| 49 | $R^1 + R^2 = (CH_2)_3$ | | $R^3 + R^4 = (CH_2)_3$ | | H | $(CH_2)_2CONHNH_2$ | H | — | — |
| 50 | $R^1 + R^2 = (CH_2)_3$ | | $R^3 + R^4 = (CH_2)_3$ | | H | $(CH_2)_2CONH-$ $(CH_2)_5NH_2$ | H | — | — |
| 51 | $R^1 + R^2 = (CH_2)_3$ | | $R^3 + R^4 = (CH_2)_3$ | | H | Cl | — | $CH_2Cl$ | — |
| 52 | $R^1 + R^2 = (CH_2)_3$ | | $R^3 + R^4 = (CH_2)_3$ | | H | $C_2H_5$ | — | $CO_2H$ | — |
| 53 | $R^1 + R^2 = (CH_2)_3$ | | $R^3 + R^4 = (CH_2)_3$ | | H | Cl | — | $CO_2H$ | — |
| 54 | $R^1 + R^2 = (CH_2)_3$ | | $R^3 + R^4 = (CH_2)_3$ | | H | $(CH_2)_2CO_2H$ | — | H | — |
| 55 | $R^1 + R^2 = (CH_2)_3$ | | $R^3 + R^4 = (CH_2)_3$ | | H | $(CH_2)_4CO_2H$ | — | H | — |
| 56 | $R^1 + R^2 = (CH_2)_3$ | | $R^3 + R^4 = (CH_2)_3$ | | H | $(CH_2)_{11}CO_2H$ | — | H | — |
| 57 | $R^1 + R^2 = (CH_2)_3$ | | $R^3 + R^4 = (CH_2)_3$ | | H | $(CH_2)_2CO_2H$ | — | $CF_3$ | — |
| 58 | $R^1 + R^2 = (CH_2)_3$ | | $R^3 + R^4 = (CH_2)_3$ | | H | $(CH_2)_2CO_2H$ | — | CN | — |
| 59 | $R^1 + R^2 = (CH_2)_3$ | | $R^3 + R^4 = (CH_2)_3$ | | H | H | $CO_2H$ | — | $COCH_3$ |
| 60 | $R^1 + R^2 = (CH_2)_3$ | | $R^3 + R^4 = (CH_2)_3$ | | H | H | $CO_2Succ.$ | — | $COCH_3$ |
| 61 | $R^1 + R^2 = (CH_2)_3$ | | $R^3 + R^4 = (CH_2)_3$ | | H | Cl | $CO_2H$ | — | $COCH_3$ |
| 62 | $R^1 + R^2 = (CH_2)_3$ | | $R^3 + R^4 = (CH_2)_3$ | | H | Cl | $CO_2Succ.$ | — | $COCH_3$ |
| 63 | $R^1 + R^2 = (CH_2)_3$ | | $R^3 + R^4 = (CH_2)_3$ | | H | $R^6 + R^9 =$ $(CH_2)_2CO-$ | H | — | see $R^6$ |

[a]Succ. indicates a succinimidyl ester.

Figure 1B:
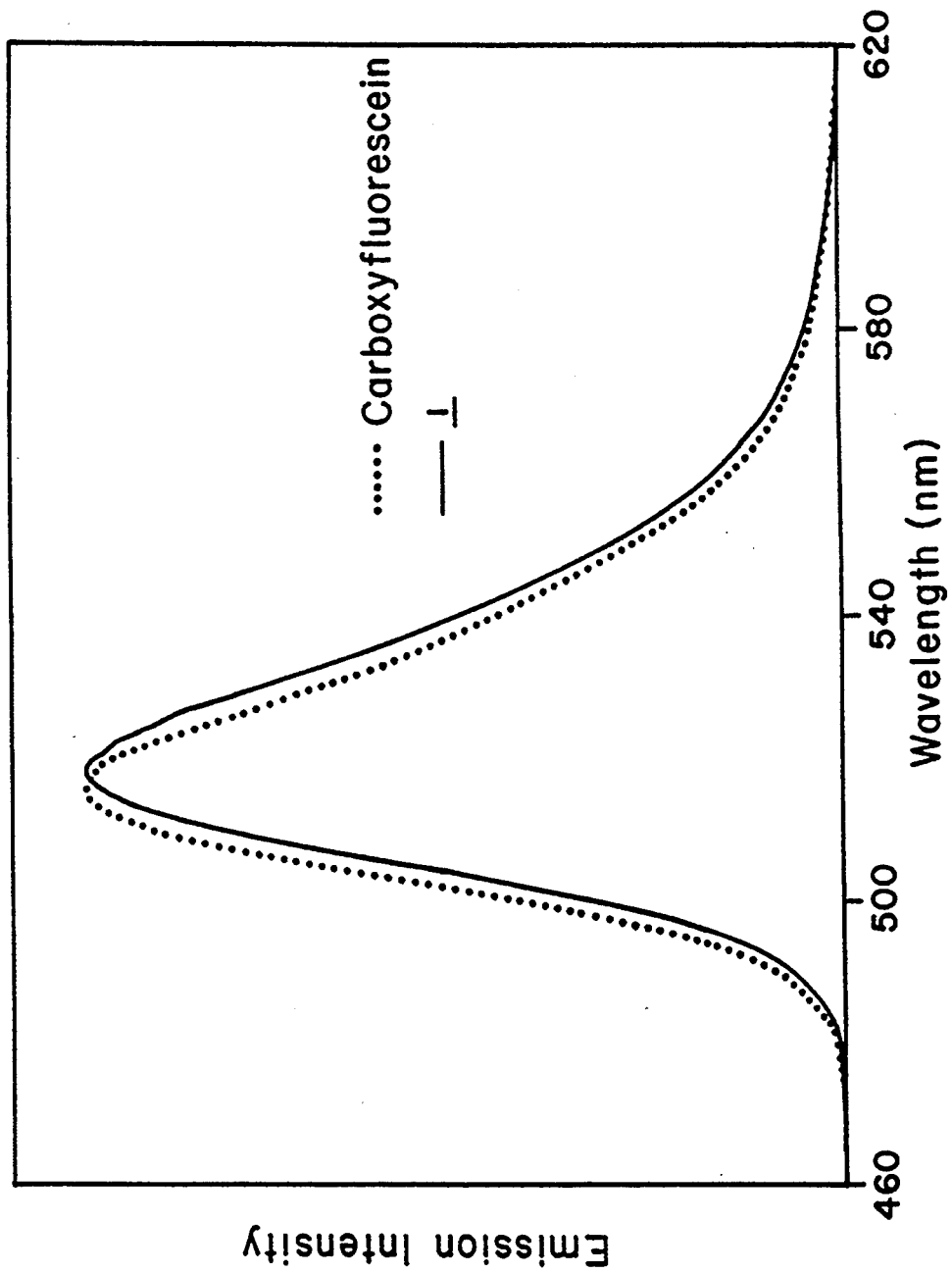
FIG. 1b shows the emission spectra of dye 1 and carboxyfluorescein in 50 mM potassium phosphate buffer at pH 8.0.
Figure 2A:
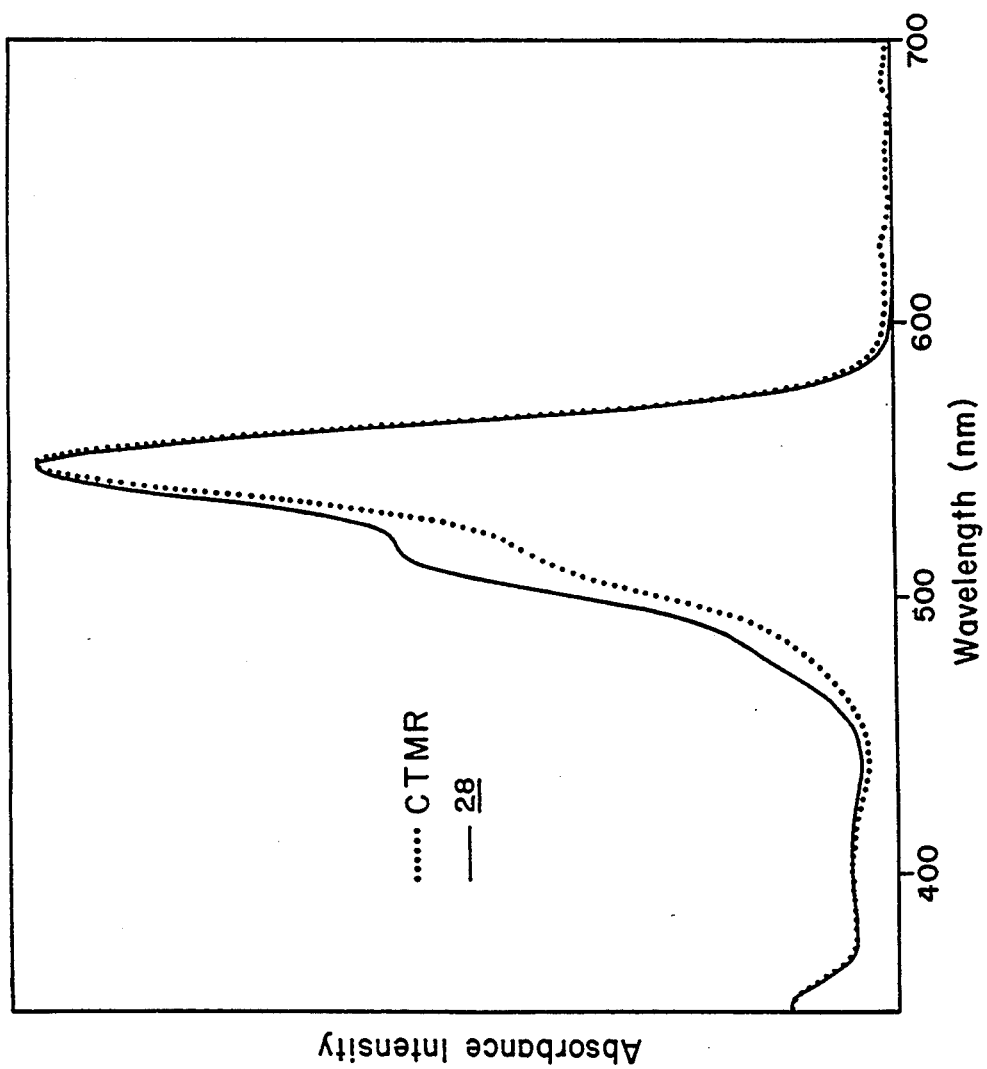
FIG. 2a shows the absorption spectra of dye 28 and carboxytetramethylrhodamine (CMTR) in 50 mM potassium phosphate buffer at pH 8.0.
Figure 2B:
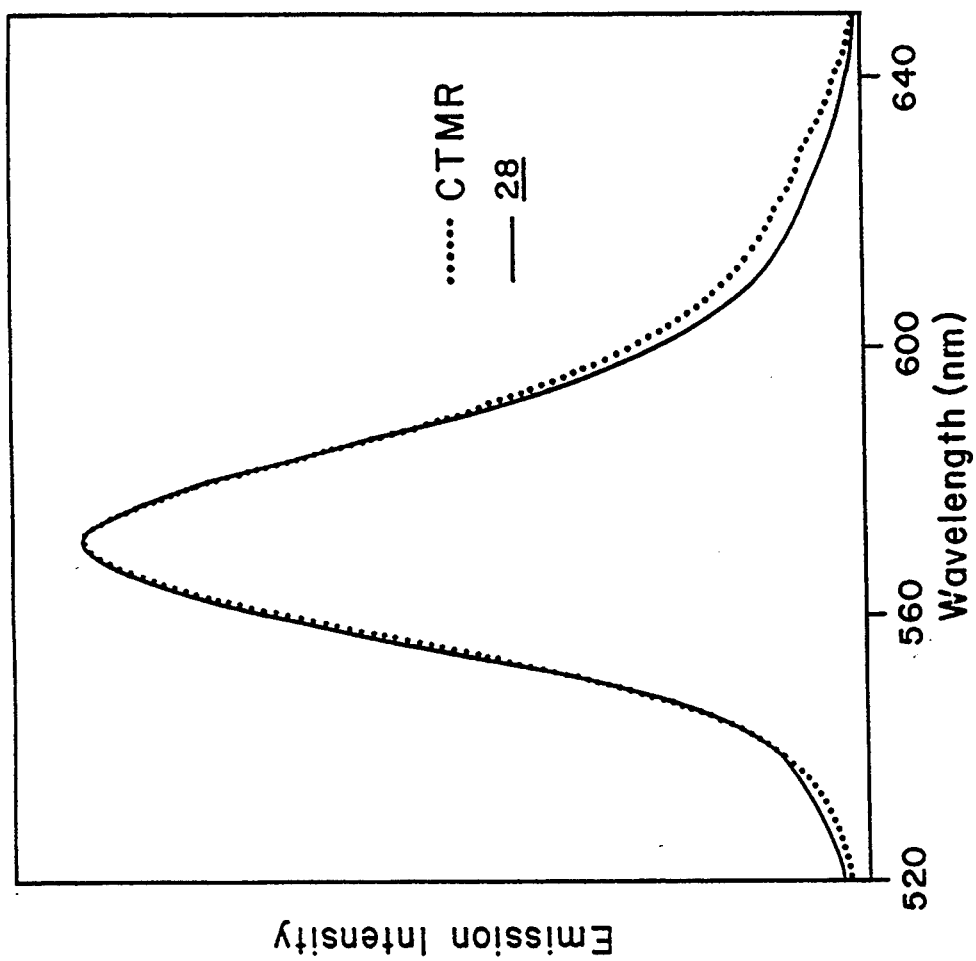
FIG. 2b shows the emission spectra of dye 28 and carboxytetramethylrhodamine (CMTR) in 50 mM potassium phosphate buffer at pH 8.0.
Figure 3:
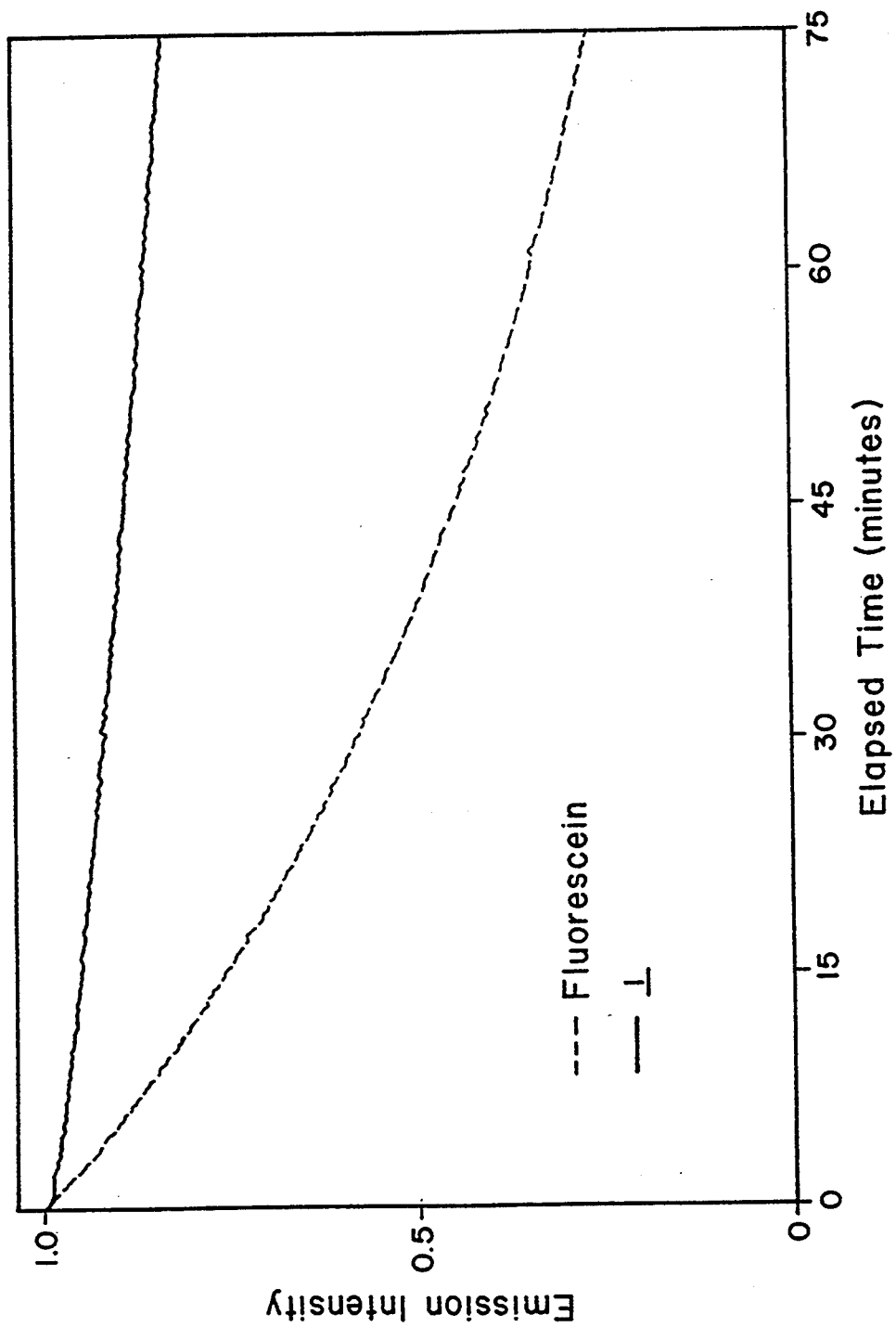
FIG. 3 shows the photobleaching of equimolar solutions of 1 and fluorescein in 50 mM potassium phosphate buffer at pH 8.0.
Figure 4A:
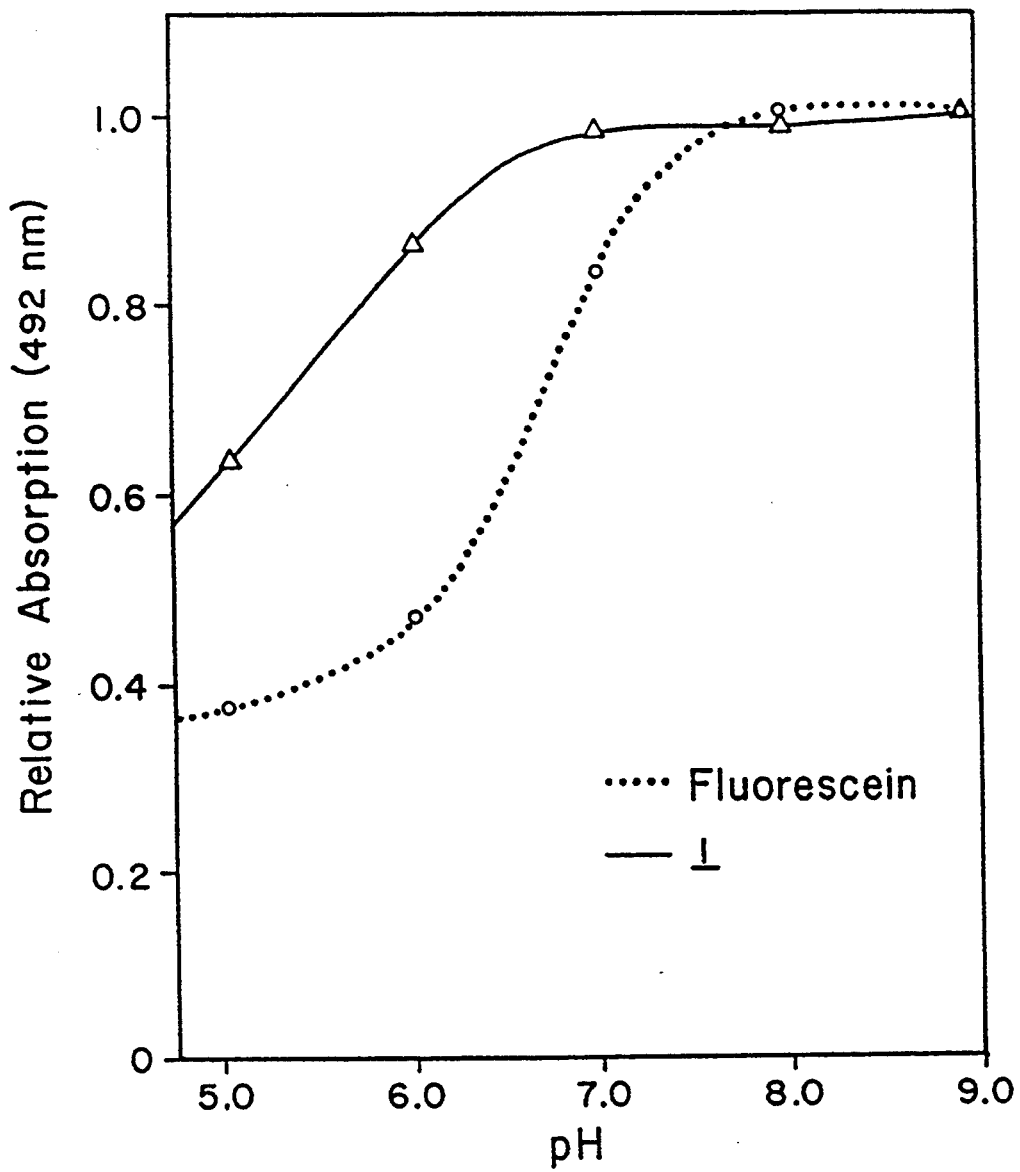
FIG. 4a shows the pH dependence of absorption intensities of dye 1 and fluorescein in 50 mM potassium phosphate buffered soutions at various pH values.
Figure 4B:
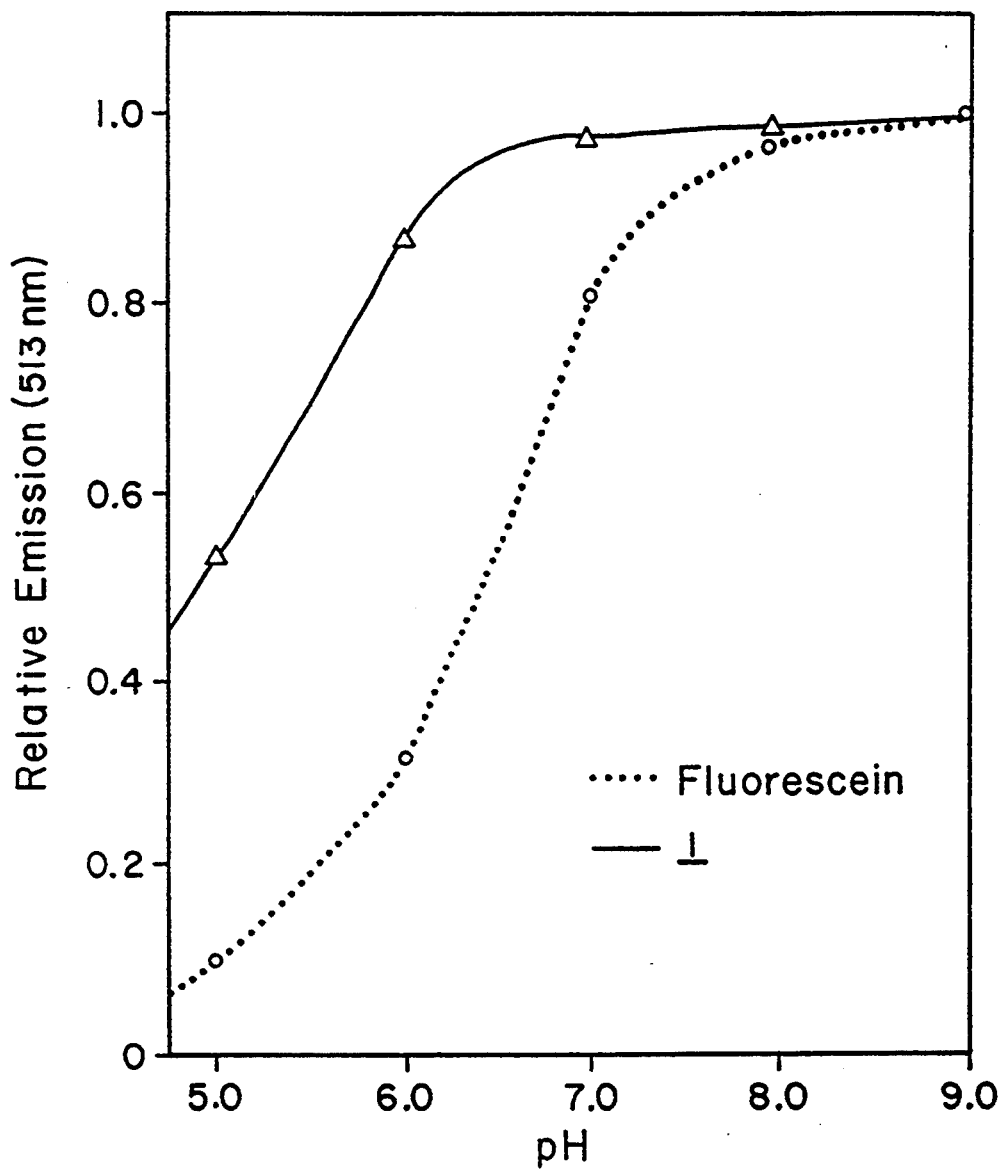
FIG. 4b shows the pH dependence of emission intensities of dye 1 and fluorescein in 50 mM potassium phosphate buffered soutions at various pH values.
Figure 5:
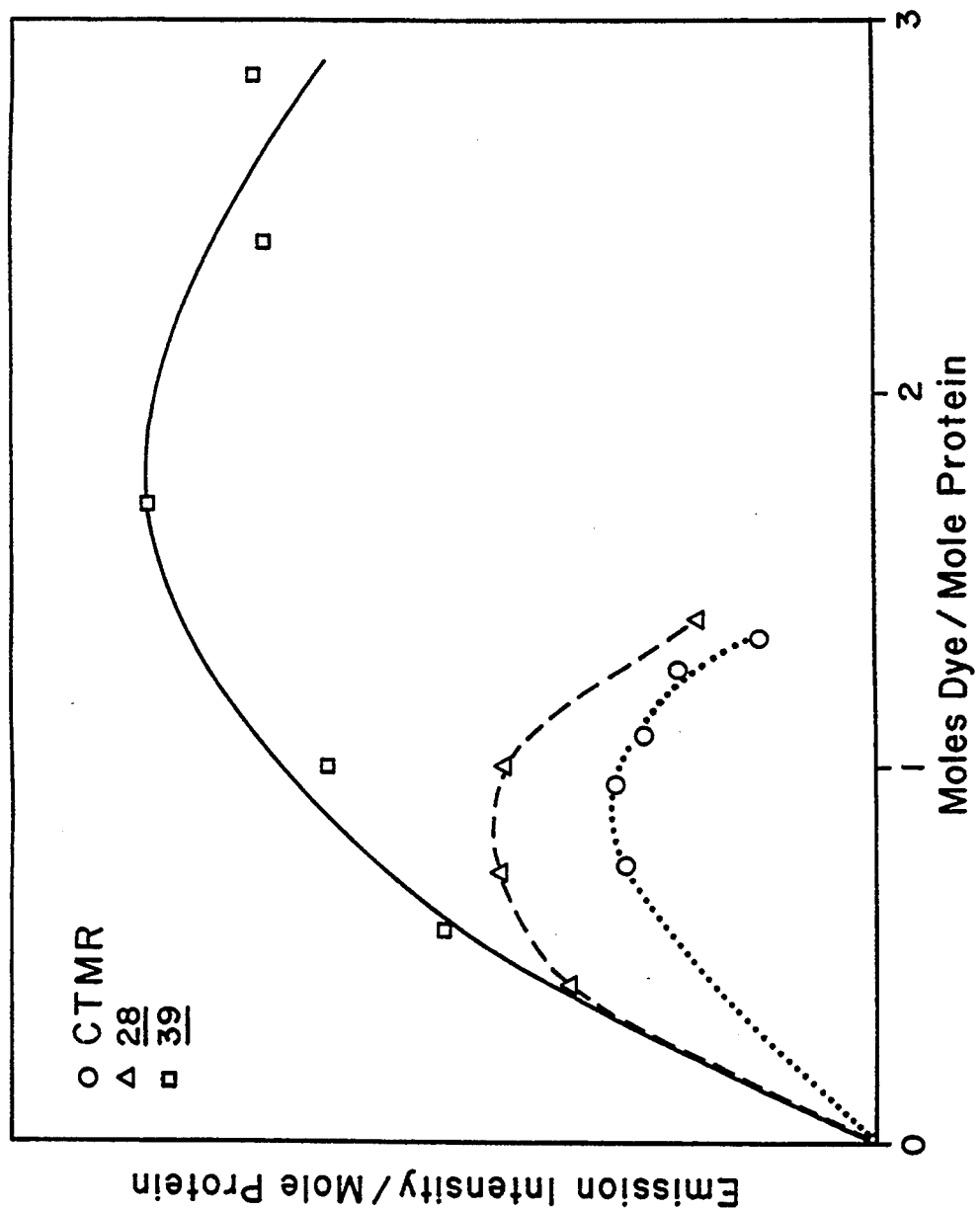
FIG. 5 shows the molar emission intensity as a function of degree of substitution for conjugates of bovine serum albumin (BSA) with carboxytetramethylrhodamine (CTMR), 28, and 39.

Absorption and emission spectra of 1 from Table 2 versus carboxyfluorescein are given in FIG. 1a and 1b. Absorption and emission spectra of a second new derivative, 28, and carboxytetramethylrhodamine (CTMR) are illustrated in FIG. 2a and 2b. Obvious are the similar wavelengths and intensities for maximum emission and similar bandwidths of the rhodol dyes and these standard fluorophores. The spectral similarity to commonly used fluorescent labels makes the dyes valuable for applications such as fluorescence microscopy, flow cytometry, DNA sequencing and other applications which require multiple dyes that are compatible with existing, commercially available filters and excitation sources. The extinction coefficients for the rhodol dyes are generally greater than 50,000 $cm^{-1} M^{-1}$ and the quantum yields of the dyes in water are generally above 0.4. The rhodol derivatives exhibit considerably slower rates of photobleaching than fluorescein derivatives, which enhances their utility in applications such as quantitative fluorometric assays and fluorescence microscopy. The superior photostability of the subject dyes relative to fluorescein derivatives is depicted in FIG. 3 for fluorescein and 1. Measurements performed with a number of rhodol derivatives indicate that high photostability is a property of the entire class rhodol derivatives described in this invention. In aqueous solution, the subject fluorophores exhibit absorption and emission spectra with less significant pH dependence between pH 6 and 10, as illustrated in FIG. 4 for 1 and fluorescein. The utility of the rhodol derivatives as fluorescent labels is illustrated in FIG. 5 for bovine serum albumin conjugates of 28, 39 and carboxytetramethylrhodamine (CTMR). These rhodol conjugates are approximately 1.5- to three-fold more fluorescent than the spectrally similar rhodamine conjugates, which increases the sensitivity of detection of the fluorescently labelled ligand. Table 3 lists the approximate spectral properties of several of the dyes that are the subject of this invention.

TABLE 3
PHYSICAL PROPERTIES OF NEW RHODOL DYES

| Compound | Abs Max[a] (nm) | $\epsilon^a$ ($\times 10^{-3}$ $M^{-1} cm^{-1}$) | Em Max[a] (nm) | QY[a,b] | $pK_a^c$ |
|---|---|---|---|---|---|
| Fluorescein | 490 | 75 | 514 | 0.92 | 6.4 |
| Carboxyfluorescein | 491 | 75 | 514 | 0.78 | 6.4 |
| Carboxytetramethylrhodamine | 547 | 77 | 574 | 0.23 | — |
| 1 | 492 | 59.9 | 517 | 0.81 | 5.59 |
| 5 | 502 | — | 524 | 0.73 | — |
| 6 | 510 | — | 535 | 0.39 | — |
| 7 | 508 | 78.1 | 533 | 0.66 | |
| 8 | 514 | 80.5 | 540 | 0.53 | 4.49 |
| 11 | 516 | 80.9 | 541 | 0.49 | — |
| 12 | 510 | 54.8 | 535 | 0.81 | 5.82 |
| 14 | 511 | 79.8 | 540 | 0.61 | — |
| 16 | 516 | 56.8 | 546 | 0.23 | — |
| 17 | 510 | 79.4 | 534 | 0.65 | 5.91 |
| 19 | 513 | — | 540 | 0.22 | — |
| 20 | 518 | — | 544 | 0.18 | — |
| 21 | 508 | — | 543 | 0.12 | — |
| 22 | 516 | 80.9 | 537 | — | 6.12 |
| 24 | 524 | — | 546 | 0.37 | 4.50 |
| 26 | 540 | 66.8 | 562 | 0.43 | — |
| 28 | 547 | 74.5 | 572 | 0.31 | 5.11 |
| 30 | 541[d] | 57.3 | 567[d] | — | — |
| 31 | 540[d] | — | 568[d] | — | — |
| 33 | 540 | 79.4 | 571 | 0.59 | — |
| 34 | 547 | — | 572 | — | — |
| | 531[d] | 84.4[d] | 562[d] | — | — |
| 37 | 542 | — | 574 | — | — |
| 39 | 541 | 58.2 | 562 | 0.41 | 6.63 |
| 42 | 544 | — | 571 | — | — |
| 43 | 545 | — | 572 | — | — |
| 44 | 544 | — | 572 | — | — |
| 45 | 544 | — | 573 | — | — |
| 48 | 543 | — | 571 | 0.40 | — |
| 49 | 542 | — | 573 | — | — |
| 50 | 543 | — | 572 | — | — |
| 51 | 563[d] | — | 578d | — | — |
| 52 | 558 | — | 603 | — | — |
| 54 | 538 | 69.5 | 562 | 0.44 | — |
| | 531[d] | 81.4[d] | 555[d] | | |
| 55 | 538 | 64.1 | 562 | — | — |
| | 532[d] | 88.7[d] | 556[d] | | |
| 56 | 532[d] | 84.4[d] | 556[d] | — | — |

TABLE 3-continued

PHYSICAL PROPERTIES OF NEW RHODOL DYES

| Compound | Abs Max[a] (nm) | $\epsilon^a$ ($\times 10^{-3}$ M$^{-1}$cm$^{-1}$) | Em Max[a] (nm) | QY[a,b] | pK$_a^c$ |
|---|---|---|---|---|---|
| 57 | 602 | — | 635 | — | |
|  | 593[d] | — | 633[d] | | |
| 58 | 640 | — | 664 | — | — |

[a]In aqueous 50 mM phosphate buffer at pH 8.0–9.0, unless otherwise specified
[b]Uncorrected
[c]In aqueous 50 mM phosphate buffer
[d]In methanol

2. Syntheses

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described.

The following synthetic examples illustrate how one of ordinary skill in the art could synthesize a variety of the chemically reactive derivatives containing the desired fluorophore that are the subject of this invention. The methods outlined are intended to be illustrative and not to define or limit the possible methods of dye synthesis. It is also to be recognized that the specific compounds described herein are included for the purpose of clearly demonstrating the nature of the invention and do not exhaust the structural and chemical variations which are also considered to fall within the scope of this invention. It is to be understood that certain changes and modifications which are apparent to one skilled in the art are included in the purview and intent of this invention. Inclusion of spectral and other characterization of some of the synthetic products and intermediates in Tables 2 and 4 is intended to facilitate comparison and confirmation of products by one skilled in interpretation of spectral techniques and not to specifically define limitations or absolute values for physical properties of the materials.

In general, the synthetic step of the procedure that results in formation of the new rhodol fluorophores that are the subject of this invention is condensation of a substituted or unsubstituted resorcinol with a substituted or unsubstituted 6-acyl-3-aminophenol in the presence of a Lewis acid catalyst such as zinc chloride or a dehydrating acid such as polyphosphoric acid or sulfuric acid. Alternatively, the same products can be prepared by condensing a substituted or unsubstituted amino phenol with a substituted or unsubstituted 4-acylresorcinol in the presence of a Lewis acid catalyst. Subsequent modifications of the dyes before or after purification give the esters, ethers, amides and other derivatives that are also considered part of this invention. Table 2 gives a tabulation of several examples of novel rhodol derivatives that have been prepared.

4-Acylresorcinols of utility for preparing reactive rhodols are conveniently prepared by treatment of fluorescein or substituted fluoresceins, including but not limited to, 4',5'-dimethylfluorescein, 2',7'-dichlorofluorescein, 2',7'-bis(carboxyethyl)-5-(and -6)carboxyfluorescein (BCECF), 5-(and-6)carboxyfluorescein (mixed or separated isomers) and 5-(and -6)aminofluorescein with strong base at an elevated temperature [N. N. Ghatak & S. Dutt, *J. Indian Chem. Soc.* 6, 19 (1929)] or by condensation of resorcinol or a substituted resorcinol with phthalic anhydride, a substituted phthalic anhydride or other anhydrides or acid chlorides under approximately equimolar conditions.

6-Acyl-3-aminophenols (or substituted amino) can be prepared by an analogous hydrolysis of a symmetrical rhodamine dye including but not limited to rhodamine B, rhodamine 6G, carboxytetraalkylrhodamine, rhodamine 101, or 5-(or-6)-aminotetraalkylrhodamine or such, with strong base at an elevated temperature. Alternatively, 6-acyl-3-dialkylaminophenols can be prepared by acylation of a dialkylaminophenol with one equivalent of an acid chloride or anhydride [Ger. Often. 3,018,546].

Another method for synthesis of some rhodol derivatives consists of condensation of a substituted or unsubstituted 3-aminophenol with an appropriately substituted phthalic acid or anhydride to give a symmetrical rhodamine which is subsequently hydrolyzed under acidic or basic conditions to yield the corresponding rhodol. Frequently there are alternative synthetic routes whose choice depends primarily on the availability or ease of synthesis of the reactants and acyl intermediates.

Suitable substituents on the aminophenols or resorcinols include but are not limited to hydrogen, halogen, alkyl, and acyl. Useful aminophenols include those that contain 5- or 6-membered rings between the nitrogen and the positions ortho to the nitrogen (e.g. julolidines, tetrahydroquinolines and dihydroindoles) and ring-containing precursors such as m-morpholinophenol. When there are available unsubstituted positions on the aromatic rings of the rhodol dyes they may be modified after they are formed by reactions that include halogenation, alkylation, nitration and sulfonation. The reactive derivatives of the rhodol dyes that are the subject of this invention, including the functional groups listed in Table 1, can be prepared subsequent to preparation of the novel amine, carboxylic acid or sulfonic acid containing rhodols described in this invention by use of many essentially equivalent reactions familiar to one skilled in the art. Examples of methods that are suitable for preparation of selected members of this new class of reactive dyes are given in the examples outlined below. It is recognized that variations in the synthetic methods and reactants are possible that would fall within the scope and intent of this invention.

a. Preparation of 5-(and -6)-carboxy-2',7'-dimethyl-3'-hydroxy-6'-N-ethylamino-spiro[isobenzofuran-1(3H),9'-[9H]xanthen-3-one (12)

A solution of 10 g 5-(and -6)-carboxy-N,N'-diethyl-2',7'-dimethylrhodamine in 150 ml 2M potassium hydroxide in methanol and 75 ml water was refluxed four days. After cooling, most of the methanol was removed by evaporation under reduced pressure, the mixture was diluted to approximately 500 ml with water and washed with 3×500 ml chloroform. The aqueous phase was filtered and acidified with concentrated hydrochloric acid. The solid was collected, dried and chromatographed over silica gel in 10:2:88 methanol:triethylamine:chloroform. The combined, evaporated product containing fractions were dissolved in water and acidified with concentrated hydrochloric acid. The precipitated dye was collected and dried to give 3 g red-orange powder.

b. Preparation of 3'-hydroxy-2.3,6,7-tetrahydro-1H, 5H-quinolizino[1,9-hi]-spiro[isobenzofuran-1(3H),9'-[9H]xanthen-3-one-2'-(3-propionic acid) (39)

To a stirred solution of 3.0 g 9-(2'-carboxybenzoyl)-8-hydroxyjulolidine (prepared by equimolar condensation of 8-hydroxyjulolidine and trimellitic anhydride) in 25 ml concentrated sulfuric acid was added 3.0 g 4-(2'-carboxyethyl)-resorcinol, methyl ester. The mixture was stirred for 45 min., then 1 ml water was added. After stirring for an additional two hours, the product was precipitated by addition of a solution of 30 g sodium hydroxide in 600 ml water. The solid was collected by filtration and dried. The crude product was purified by chromatography over silica gel in 10:2:88 methanol: triethylamine: chloroform. The combined, evaporated, product containing fractions were dissolved in water and acidified with concentrated hydrochloric acid. The precipitated dye was collected and dried to give 3.1 g red-orange powder.

c. Preparation of 5-(and -6)-carboxy-2'-chloro-3'-hydroxy-1,2,3,4-tetrahydropyridino[5,6-i]-spiro[isobenzofuran-1(3H),9'-[9H]xanthen-3-one (24)

A mixture of 124 mg 4-chloro-6-(2',4'-(and -2',5')-dicarboxybenzoyl)-resorcinol (prepared by hydrolysis of 5-(and -6)-carboxy-2',7'-dichlorofluorescein in 25% sodium hydroxide at reflux), 105 mg 7-hydroxy-1,2,3,4-tetrahydroquinoline (prepared by hydrogenation of 7-hydroxyquinoline) and 240 mg zinc chloride were heated in an oil bath at 185°–195° C. for five hours. The crude product was dissolved in 5% (w/v) aqueous sodium hydroxide, filtered, and the filtrate was acidified with concentrated hydrochloric acid. The solid was collected, dried and purified by chromatography over silica gel using a stepwise gradient of 5:1:44 methanol: triethylamine: chloroform to 10:1:39 methanol: triethylamine: chloroform. The combined and evaporated product-containing fractions were dissolved in water and acidified with concentrated hydrochloric acid. The solid was collected and dried to give 74 mg yellow-orange powder.

d. Preparation of 5-(and -6)-carboxy-3'-hydroxy-6'-trifluoroacetamido-spiro[isobenzofuran-1(3H),9'-[9H]xanthen-3-one, succinimidyl ester (4).

Trifluoroacetic anhydride (3 g) was added to a stirred suspension of 0.66 g 5-(and -6)-carboxy-3'-hydroxy-6'-amino-spiro[isobenzofuran-1(3H,9'-[9H]xanthen-3-one (1) in 50 ml ethyl acetate. After 30 min., 2.4 g N-hydroxysuccinimide was added to the resulting pale orange solution, followed by addition of 4.75 g pyridine in 10 ml ethyl acetate. The mixture was stirred three hours, then diluted to approximately 100 ml with ethyl acetate, acidified with trifluoroacetic acid and washed with 3×150 ml cold water. The ethyl acetate was dried and evaporated under reduced pressure. The residue was triturated with toluene and the solid collected to give 0.68 g yellow solid. The filtrate was concentrated to give 0.24 g additional product.

e. Preparation of N-(3'-hydroxy-2,3,6,7-tetrahydro-1H, 5H-quinolizino[1,9,hi]-spiro[isobenzofuran-1(3H) ,9'-[9H]xanthen-3-one-2'-(3-propionyl) )-cadaverine (50)

To a suspension of 300 mg 3'-hydroxy-2,3,6,7-tetrahydro-1H, 5H-quinolizino[1,9-hi]-spiro[isobenzofuran-1(3H),9'-[9H]xanthen-3-one-2'-(3-propionic acid) (39) in 5 ml dimethylformamide was added 107 mg 4-dimethylaminopyridine followed by 150 mg disuccinimidyl carbonate. After stirring for one hour, 130 mg additional disuccinimidyl carbonate was added. The mixture was stirred for one more hour and 3.5 ml of the resulting solution was added to a solution of 1.0 ml cadaverine in 10.0 ml methanol. After one hour, the solution was evaporated. The crude product was purified by chromatography over silica gel in 25:2:73 methanol: triethylamine: chloroform. The combined, product containing fractions were evaporated to give 232 mg 50 as the triethylammonium salt. The hydrazide derivative 49 was prepared in an analogous manner.

f. Preparation of N-(3'-hydroxy-2,3,6,7-tetrahydro-1H, 5H-quinolizino[1.9-hi]-spiro[isobenzofuran-1(3H),9'-[9H]xanthen-3-one-2'-(3-propionyl))-N'-(4-azidobenzoyl)-cadaverine (43)

To a solution of 50 mg N-(3'-hydroxy-2,3,6,7-tetrahydro-1H, 5H-quinolizino[1,9-hi]-spiro[isobenzofuran-1(3H) ,9'-[9H]xanthen-3-one-2'-(3-propionyl))-cadaverine (50) in 1.0 ml methanol was added 38 mg succinimidyl 4-azidobenzoate in 1 ml chloroform. The mixture was stirred overnight at room temperature then evaporated. The crude product was purified by chromatography over silica gel in 5:1:94 methanol:triethylamine:-chloroform to give 36 mg 43 as the triethylammonium salt. The iodoacetamide 44 from succinimidyl iodoacetate, the acrylamide 42 from succinimidyl acrylate, the aldehyde 46 from succinimidyl 4-formylphenoxyacetate and the maleimide 45 from succinimidyl maleimidylacetate were prepared in an analogous manner.

g. Preparation of 3'-hydroxy-9'-trifluoromethyl-2,3,6,7-tetrahydro-1H, 5H-quinolizino[1,9-hi]-[9'-yl-(3H)-xanthen-2'-(3-propionic acid) (56)

To a solution of 101 mg 8-hydroxy-9-trifluoroacetyl-julolidine [N. F. Haley, J. Heterocyclic Chem. 14, 683 (1977)] in 1.0 ml concentrated sulfuric acid was added 03 mg 4-carboxyethylresorcinol, methyl ester. The mixture was stirred at room temperature for two hours. Five drops of water were added and the mixture was stirred overnight to hydrolyze the ester. The reaction mixture was added dropwise to saturated sodium bicarbonate and washed with chloroform. The aqueous phase was acidified with acetic acid and cooled to 4° C. for two hours. The solid was collected and dried to give 88 mg of a blue powder.

3. Methods for Characterization of the Rhodol Dyes

Stock solutions were prepared by accurately weighing and dissolving 5–10 mg samples of the compounds in 50 mM potassium phosphate buffer at pH 8.0. Absorbance solutions were prepared by further diluting the stock solution with 50 mM potassium phosphate buffer at pH 8.0. Absorption data was collected on an IBM Model 9420 UV/Visible Spectrophotometer and extinction coefficients were determined by standard Beer's Law calculations.

Uncorrected fluorescence data was obtained on a Perkin-Elmer Model 650-40 Fluorescence Spectrophotometer equipped with a Perkin-Elmer/Hitachi 057 X-Y recorder using a ten- to twentyfold dilution of the absorbance solutions. Fluorescence of the rhodol dyes was determined for the reactive dyes and for their conjugates with model compounds by dissolving the dye at a concentration above $1 \times 10^{-8}$M in an appropriate solvent such as water, methanol or chloroform, followed by measurement of the fluorescence in a suitable instrument, such as a fluorescence spectrometer or fluorescence microscope. Results of the spectral determination for some of the dyes are tabulated in Table 3. Fluorescence could also be observed for the dyes in solution by visual inspection with illumination by a suitable source.

An estimate of the quantum yield of the dyes relative to fluorescein (quantum yield=0.92 in 0.01M sodium hydroxide) was obtained by integrating the emission spectrum of the dye excited at the same wavelength and optical density as the standard. Approximate quantum yields of a number of rhodol dyes are tabulated in Table 4. Approximate photostabilities of the rhodol derivatives, relative to fluorescein, were determined by measuring the time dependent decrease in fluorescence intensity, during continuous illumination, of equimolar solutions of the rhodol dyes and fluorescein.

The purity of the dyes was determined by HPLC analysis of 15 μl aliquots of solutions containing the compounds dissolved in 3:1 methanol: 50 mM triethylammonium acetate buffer (pH 7.1). HPLC analysis was performed with a Waters system consisting of a model 600E multisolvent delivery pump, a model 700 WISP automated injector and a Maxima 820 chromatography workstation. The detector was set at 254 nm. Samples were eluted from a Brownlee Labs 220×4.6 mm Spheri-5 $C_{18}$ (5 μm particle size) column with a gradient of 50 mM triethylammonium acetate buffer (pH 7.1) and methanol (0–60% methanol in 30 min.) at a flow rate of 1 ml/min. and an initial pressure of 1700 psi. Samples were detected by absorbance at 400 nm and purity was calculated by integration of this absorbance. Results of these analyses are summarized in Table 4. The spectroscopic data and chemical reactivity of the compounds were consistent with the structural assignments reported here.

TABLE 4

HPLC of Rhodol Derivatives

| Compound[a] | Isomer | $R_t$ (min) | Purity (%) |
|---|---|---|---|
| 1 | a. + b. | 3.91 + 5.19 | 100 |
| 7 | a. | 6.34 | 99.3 |
|   | b. | 11.79 | 94.3 |
| 8 | a. + b. | 5.80 + 12.01 | 91.3 |
|   | a. + b. | 5.20 + 11.79 | 96.0 |
|   | a. + b. | 5.25 + 12.10 | 98.4 |
| 11 | a. | 5.83 | 99.9 |
|   | b. | 12.71 | 94.9 |
| 12 | a. | 6.94 | 95.7 |
|   | b. | 12.86 | 83.5 |
| 14 | a. | 5.20 | 98.7 |
|   | b. | 13.53 | 95.3 |
| 16 | a. | 8.41 | 99.7 |
|   | b. | 14.18 | 100 |
| 17 | — | 17.76 | 92.0 |
| 24 | a. | 5.63 | 100 |
| 26 | a. | 11.28 | 99.7 |
|   | b. | 17.07 | 99.2 |
| 28 | a. | 13.34 | 100 |
| 32 | a. | 13.62 | >90 |
| 33 | a. | 15.51 | 100 |
| 34 | b. | 21.37 | 89.0 |
| 34 | a. | 32.43 | 93.7 |
| 37 | — | 19.15 | 71.2 |
| 39 | — | 23.55 | 95.6 |
| 42 | — | 22.62 | 100 |
| 43 | — | 25.83 | 79.8 |
| 45 | — | 20.52 | 91.7 |
| 52 | — | 17.65 | 78.9 |
| 54 | — | 21.55 | 93.5 |
| 55 | — | 23.48 | 94.1 |
| 56 | — | 32.47 | 93.5 |

[a]For derivatives which contain isomeric carboxylic acids at the 5- and 6- positions, the designation used is a. 6-carboxy, b. 5-carboxy and a. + b. mixed 5-carboxy and 6-carboxy isomers.

4. Determination of the Chemical Reactivity of Rhodol Dyes

The chemical reactivity of the dyes that are the subject of this invention was determined by incubation of the reactive derivatives in aqueous, methanolic, or dimethylsulfoxide solution with model compounds. Their reactivity was demonstrated by thin layer chromatography in a solvent that separated the reactive dye from its products with visual detection of the fluorescence emission or by HPLC with photometric detection. It was demonstrated that 1-aminobutane reacts to form new products with derivatives such as 2, 4, 9, 13, 15, 23, 25, 27, 29, and 63, that aminodextran reacts with 2, 9 and 23, that bovine serum albumin, alphabungarotoxin and phallacidin react with activated esters such as 2, 4, 9, 29 and 63 to give fluorescent peptide or protein conjugates, that 2-mercaptoethanol reacts with 35 and 44, that 50 reacts with succinimidyl iodoacetate, succinimidyl 4-formyl benzoate, S-acetyl mercapto succinic anhyride, succinimidyl maleimidylacetate, succinimidyl acrylate and succinimidyl 4-azidobenzoate to form 44, 45, 46, 47, 41 and 43, respectively, that acetone reacts with 49, and that 39 reacts in the presence of N,N'-dicyclohexylcarbodiimide to give the lactone 63 which reacts with amines and hydrazine to give 50 and 49, respectively. Furthermore, it was demonstrated that the esters such as 9 can react with hydrazine to give hydrazides and with amines to give amides such as 36, and 31. Additionally, removable protecting groups, such as trifluoroacetamide as in 3 and 4, and acetate as in 59, 60, 61, and 62, may be incorporated into the dyes and removed subsequent to reaction with a ligand of interest.

The conjugates can be used to trace the presence of particular structure in a biological system according to methods currently used in the art. One of the dyes described herein is reacted with a ligand capable of binding to at least one type of target biomolecule in the biological structure to form a fluorescent conjugate of the fluorescent dye and the ligand. The fluorescent conjugate is added to the system and allowed to bind to target biomolecules within the system. Upon binding with the fluorescent conjugates, the target biomolecules are rendered fluorescent. The system or a portion of the system is illuminated with light containing a wavelength capable of causing the fluorescent target biomolecules to fluoresce. The illuminated system is then examined in a manner to permit detection of the fluorescent target biomolecules.

Having illustrated and described the principles of our invention in a number of specific embodiments, it should be apparent to those of ordinary skill in the art that such embodiments may be modified in detail without departing from such principles. We claim as our invention all such modifications as come within the true spirit and scope of the following claims.

What is claimed is:

1. A compound comprising a fluorescent dye having the structure

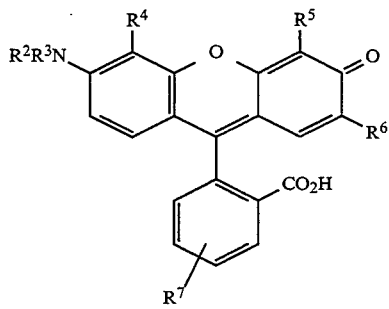

wherein $R^1$ is H or $CH_3$, and $R^2$ is H, $CF_3CO$, $CH_3$, or $C_2H_5$; or $R^1$ in combination with $R^2$ is $(CH_2)_3$;
$R^3$ is H, $CH_3$, or $C_2H_5$, and $R^4$ is H; or $R^3$ in combination with $R^4$ is $(CH_2)_3$;
$R^5$ is H, $CH_2NH_2$, $CH_2NHCOCH_2Cl$, $CH_2NHCOCH_2I$; $CH_2NHCOCH=CH_2$, or $CH_2NHCOC_6H_4N_3$;
$R^6$ is H, Cl, Br, $CH_3$, or $C_2H_5$, or $(CH_2)_nCH_3$ where n is an integer from 0 to 15, or $(CH_2)_nCO_2H$, where n is an integer from 0 to 11;
$R^7$ is H, $CO_2H$,

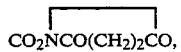

$NH_2$, NCS, $CH_2NHCOCH_2Cl$, or $CH_2NHCOCH_2I$; such that $R^7$ is not H if $R^5$ is H;
conjugated to a reactive site on a biomolecule via reaction of a chemically reactive functional group on the dye with a reactive site on the biomolecule.

2. A compound as claimed in claim 1, wherein $R^7$ is not H.

3. A compound, as claimed in claim 1, wherein one of $R^5$ and $R^6$ is a chemically reactive functional group.

4. A compound comprising a fluorescent dye having the structure

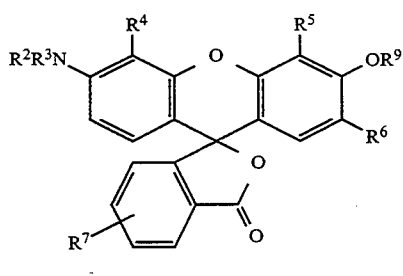

wherein
$R^1$ arid $R^4$ are independently hydrogen, alkyl, carboxyalkyl, aminoalkyl, halogen or alkoxy, the alkyl portions of which contain less than 4 carbons;
$R^2$ and $R^3$ are independently hydrogen, methyl or ethyl, or trifluoroacetyl; or
$R^1$ in combination with $R^2$, or $R^3$ in combination with $R^4$ are $(CH_2)_3$;
$R^5$ is H:
$R^6$ is H, Cl, Br. $CH_3$, or $C_2H_5$, and $R^9$ is $COCH_3$; or $R^6$ and $R^9$ in combination are $(CH_2)_2CO$;

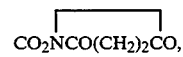

such that $R^7$ is is not H if $R^9$ is $COCH_3$;
conjugated to a reactive site on a biomolecule via reaction of a chemically reactive functional group on the dye with a reactive site on the biomolecule.

5. A compound as claimed in claim 4, wherein the biomolecule is a peptide, a protein, a hormone, a drug a nucleotide, an oligonucleotide, a nucleic acid, a polysaccharide, or a lipid.

6. A compound as claimed in claim 4, where the fluorescent dye is conjugated to a biomolecule that is a nucleotide, oligonucleotide, or nucleic acid, 7. A compound as claimed in claim 4, wherein
$R^1$ in combination with $R^2$, and $R^3$ in combination with $R^4$ are $(CH_2)_3$; and
$R^7$ is selected from the group consisting of $CO_2H$ and

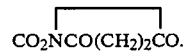

8. A compound as claimed in claim 7, wherein
$R_1$ in combination with $R^2$, and $R^3$ in combination with $R^4$ are $(CH_2)_3$;
$R^5$ is H;
$R^7$ is selected from the group consisting of $CO_2H$ and

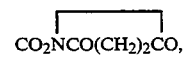

and $R^6$ and $R^9$ in combination are $(CH_2)_2CO$.

9. The compound of claim 1 formed when the fluorescent dye is conjugated to a reactive site on a biomolecule via reaction of the chemically reactive functional group with the reactive site on the biomolecule, the reactive site selected from the group consisting of amines, thiols, alcohols, phenols, aldehydes, ketones, carboxylic acids, alkyl halides, imidazoles, and olefins.

10. A compound, as claimed in claim 1, wherein the biomolecule is a peptide, a protein, a hormone, a drug, a nucleotide, an oligonucleotide, a nucleic acid, a polysaccharide, or a lipid.

11. The compound of claim 3, where the fluorescent dye is conjugated to a biomolecule that is a peptide, a protein, a nucleotide, oligonucleotide, or nucleic acid.

12. The compound of claim 4, where the fluorescent dye is conjugated to a biomolecule that is a peptide or a protein.

13. A compound of the formula; dye-biomolecule wherein said dye is fluorescent dye of the formula:

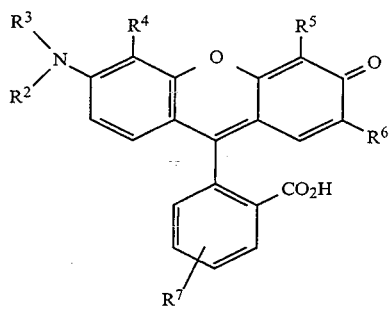

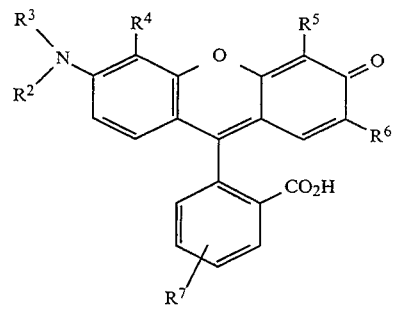

that is covalently attached to said biomolecule through a linkage that is amine, amide, carboxamide, sulfonamide, propionamide, glycineamide, amidine, imine, imide, imidazole, hydrazide, hydrazone, urea, thiourea, urethane, ester, ether, or thiother at one of the positions $R^1$ through $R^7$; and at the positions where the biomolecule is not attached:

$R^1$ is H or $CH_3$ and $R^2$ is H $CF_3CO$ $CH_3$ or $C_2H_5$; or $R^1$ in combination with $R^2$ is $(CH_2)_3$;

$R^3$ is H, $CH_3$, or $C_2H_5$, and $R^4$ is H; or $R^3$ in combination with $R^4$ is $(CH_2)_3$;

$R^5$ is H $CH_2NH_2$ $CH_2NHCOCH_2Cl$, $CH_2NHCOCH_2I$; $CH_2NHCOCH=CH_2$, or $CH_2NHCOC_6H_4N_3$;

$R^6$ is H, Cl, Br, or $(CH_2)_nCH_3$ where n is an integer from 0 to 15, or $(CH_2)_nCO_2H$, where n is an integer from 0 to 11;

$R^7$ is H, $CO_2H$,

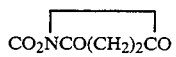

$NH_2$ NCS $CH_2NHCOCH_2Cl$, or $CH_2NHCOCH_2I$.

14. A compound, as claimed in claim 13, wherein the biomolecule X is a peptide, a protein, a hormone, a drug, a nucleotide, an oligonucleotide, a nucleic acid, a polysaccharide, or a lipid.

15. A compound, as claimed in claim 13, wherein said dye has the formula:

wherein the biomolecule is attached at one position $R^5$, $R^6$, or $R^7$; and at the positions where the biomolecule is not attached:

$R^1$ is H or $CH_3$, and $R^2$ is H, $CF_3CO$, $CH_3$, or $C_2H_5$; or $R^1$ in combination with $R^2$ is $(CH_2)_3$;

$R^3$ is H, $CH_3$, or $C_2H_5$, and $R^4$ is H; or $R^3$ in combination with $R^4$ is $(CH_2)_3$;

$R^5$ is H, $CH_2NH_2$, $CH_2NHCOCH_2Cl$ $CH_2NHCOCH_2I$; $CH_2NHCOCH=CH_2$ or $CH_2NHCOC_6H_4N_3$;

$R^6$ is H, Cl, Br, or $(CH_2)_nCH_3$ where n is an integer from 0 to 15, or $(CH_2)_nCO_2H$ where n is an integer from 0 to 11;

$R^7$ is H, $CO_2H$

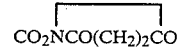

$NH_2$, NCS $CH_2NHCOCH_2Cl$, or $CH_2NHCOCH_2I$; such that $R^7$ is not H if $R^5$ is H.

16. A compound, as claimed in claim 15, wherein the biomolecule X is attached at one position $R^5$ or $R^6$ by an amide linkage.

17. A compound, as claimed in claim 15, wherein the biomolecule X is attached at $R^7$ by an amide, urea or thiourea linkage.

18. A compound, as claimed in claim 13, wherein the biomolecule X is attached at one position $R^6$ or $R^7$; and at the positions where the biomolecule is not attached: $R^1$ is H or methyl; $R^2$ and $R^3$ are independently H or $(C_1-C_2)$ alkyl; $R^4$ and $R^5$ are H; $R^6$ is hydrogen, Cl, Br, or $(C_1-C_{16})$ alkyl; and $R^7$ is hydrogen.

19. A compound, as claimed in claim 13, wherein the biomolecule X is attached at one position $R^6$ or $R^7$; and at the positions where the biomolecule is not attached: $R^1$ in combination with $R^2$ and $R^3$ in combination with $R^4$ are each $(CH_2)_3$; $R^5$ is H; $R^6$ is hydrogen, Cl, Br, or $(C_1-C_{16})$ alkyl; and $R^7$ is hydrogen.

20. A compound, as claimed in claim 13, wherein the biomolecule X is a peptide or protein that is attached at $R^7$ by an amide linkage; and at the positions where the biomolecule is not attached: $R^1$ and $R^4$ are independently hydrogen; $R^2$ and $R^3$ are independently hydrogen or $(C_1-C_2)$ alkyl; or $R^1$ in combination with $R^2$ and $R^3$ in combination with $R^4$ are each $(CH_2)_3$; and $R^5$ and $R^6$ are independently hydrogen.

* * * * *

UNITED STATES PATENT AND TRADEMARK OFFICE
CERTIFICATE OF CORRECTION

PATENT NO. : 5,442,045
DATED : August 15, 1995
INVENTOR(S) : Haugland et al.

It is certified that error appears in the above-indentified patent and that said Letters Patent is hereby corrected as shown below:

Column 7
In Table 2, the description of $R^3$ and $R^4$ for Dye 29 should read --$R^3 + R^4 = (CH_2)_3$--

At Column 13, Line 1, "3'-hydroxy-2.3,6,7-tetrahydro-1H," should read --3'-hydroxy-2,3,6,7-tetrahydro-1H,--

At Column 14, Line 49, "03 mg" should read --103 mg--

At Column 16, Line 47, "as 36," should read --as 30--

At Column 17, Lines 12-24, the formula should appear as follows:

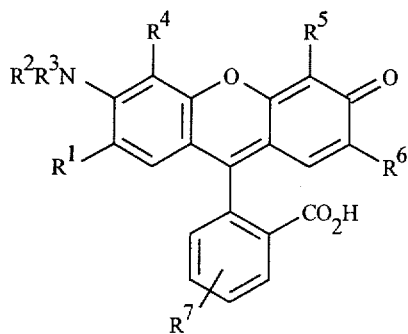

UNITED STATES PATENT AND TRADEMARK OFFICE
CERTIFICATE OF CORRECTION

PATENT NO. : 5,442,045
DATED : August 15, 1995
INVENTOR(S) : Haugland et al.

It is certified that error appears in the above-indentified patent and that said Letters Patent is hereby corrected as shown below:

At Column 17, Lines 54-64, the formula should appear as follows:

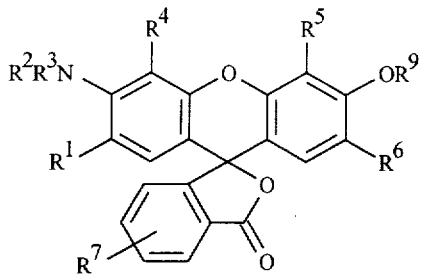

At Column 18, Line 6, "H, Cl, Br. $CH_3$" should read --H, Cl, Br, $CH_3$--

At Column 18, Line 8, insert --$R^7$ is H, $CO_2H$ or--

At Column 18, Line 19, "a drug a" should read --a drug, a--

At Column 18, Line 67, "formula;" should read --formula:--

UNITED STATES PATENT AND TRADEMARK OFFICE
CERTIFICATE OF CORRECTION

PATENT NO. : 5,442,045
DATED : August 15, 1995
INVENTOR(S) : Haugland et al.

It is certified that error appears in the above-indentified patent and that said Letters Patent is hereby corrected as shown below:

At Column 19, Lines 1-15, the formula should appear as follows:

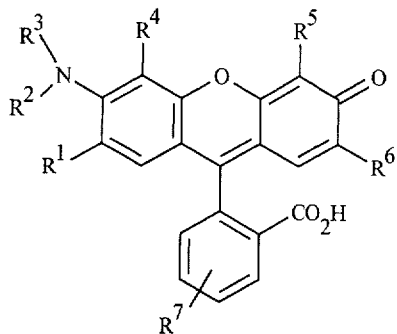

At Column 19, Line 23, "thiother" should read --thioether--

At Column 19, Line 29, "is H CF$_3$CO" should read --is H, CF$_3$CO--

At Column 19, Line 35, "H CH$_2$NH$_2$" should read --H, CH$_2$NH$_2$,--

At Column 19, Line 52, "NH$_2$ NCS CH$_2$NHCOCH$_2$Cl" should read --NH$_2$, NCS, CH$_2$NHCOCH$_2$Cl--

At Column 19, Line 55, delete "X"

UNITED STATES PATENT AND TRADEMARK OFFICE
CERTIFICATE OF CORRECTION

PATENT NO. : 5,442,045
DATED : August 15, 1995
INVENTOR(S) : Haugland et al.

It is certified that error appears in the above-indentified patent and that said Letters Patent is hereby corrected as shown below:

At Column 20, Lines 1-14, the formula should appear as follows:

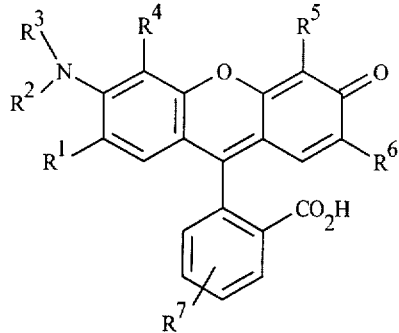

At Column 20, Line 34, "NCS CH$_2$NHCOCH$_2$Cl" should read --NCS, CH$_2$NHCOCH$_2$Cl--

At Column 20, Line 37, delete "X"

At Column 20, Line 40, delete "X"

At Column 20, Line 43, delete "X"

At Column 20, Line 49, delete "X"

At Column 20, Line 55, delete "X"

Signed and Sealed this

Tenth Day of March, 1998

Attest:

BRUCE LEHMAN

*Attesting Officer*   *Commissioner of Patents and Trademarks*